(12) United States Patent
Scarlett (10) Patent No.: US 9,488,569 B2
(45) Date of Patent: Nov. 8, 2016

(54) METHOD AND SYSTEMS TO DETECT MATTER THROUGH USE OF A MAGNETIC FIELD GRADIENT

(71) Applicant: Florida Agricultural and Mechanical University, Tallahassee, FL (US)

(72) Inventor: Carol Y. Scarlett, Tallahassee, FL (US)

(73) Assignee: Florida Agricultural and Mechanical University, Tallahassee, FL (US)

( * ) Notice: Subject to any disclaimer, the term of this patent is extended or adjusted under 35 U.S.C. 154(b) by 103 days.

(21) Appl. No.: 14/300,326

(22) Filed: Jun. 10, 2014

(65) Prior Publication Data

US 2014/0362378 A1 Dec. 11, 2014

Related U.S. Application Data

(60) Provisional application No. 61/833,076, filed on Jun. 10, 2013.

(51) Int. Cl.
*G01N 21/23* (2006.01)
*G01N 21/17* (2006.01)
*H01S 3/106* (2006.01)
*H01S 3/105* (2006.01)

(52) U.S. Cl.
CPC .......... *G01N 21/23* (2013.01); *G01N 21/1717* (2013.01); *G01N 2021/1727* (2013.01); *H01S 3/105* (2013.01); *H01S 3/106* (2013.01)

(58) Field of Classification Search
CPC ............ G01N 21/23; G01N 21/1717; G01N 2021/1727; H01S 3/105; H01S 3/106
USPC ............ 356/484, 491; 324/244.1; 359/341.3, 359/345; 372/106, 92, 98, 20–21, 93
See application file for complete search history.

(56) References Cited

U.S. PATENT DOCUMENTS

| | | | | |
|---|---|---|---|---|
| 3,831,108 A | * | 8/1974 | Le Floch | H01S 3/1398 372/31 |
| 4,205,268 A | * | 5/1980 | Eerkens | H04B 13/00 250/251 |
| 4,327,337 A | * | 4/1982 | Liu | H01S 3/305 372/108 |

(Continued)

FOREIGN PATENT DOCUMENTS

| WO | 03023409 A2 | 3/2003 |
|---|---|---|
| WO | 2004068191 A2 | 8/2004 |

(Continued)

OTHER PUBLICATIONS

Cadene, A., et al., Faraday and Cotton-Mouton effects of helium at λ=1064 nm; Physical Review A (Atomic, Molecular, and Optical Physics) 88.4 (Oct. 2013): 043815 (11.); vol. 88, Issue 4; 2 pgs.

(Continued)

*Primary Examiner* — Sang Nguyen
(74) *Attorney, Agent, or Firm* — Sutherland Asbill & Brennan LLP (57) ABSTRACT

Methods and systems for determining material composition of a test sample may be provided. The test sample may be placed in a magnetic region having a magnetic field. A light beam may be directed at the test sample in the magnetic region. A birefringence in the light beam that has passed through the test sample may be detected. The material composition of the test sample may be determined based on the detected birefringence in the light beam.

15 Claims, 4 Drawing Sheets

(56) References Cited

U.S. PATENT DOCUMENTS

| | | |
|---|---|---|
| 4,449,825 A | 5/1984 | May |
| 4,467,032 A | 8/1984 | Lowke et al. |
| 4,797,893 A | 1/1989 | Dixon |
| 4,798,952 A * | 1/1989 | Fink .................. H05H 3/02 250/251 |
| 4,812,767 A | 3/1989 | Taketomi |
| 4,907,235 A * | 3/1990 | Kuizenga ............ H01S 3/109 359/328 |
| 5,121,245 A * | 6/1992 | Johnson .............. H01S 3/117 359/285 |
| 5,142,548 A | 8/1992 | Krasinski et al. |
| 5,233,624 A * | 8/1993 | LaPlante ............ H01S 3/025 372/69 |
| 5,272,708 A | 12/1993 | Esterowitz et al. |
| 5,276,695 A | 1/1994 | Scheps |
| 5,359,621 A * | 10/1994 | Tsunoda ............ H01S 3/0975 372/55 |
| 5,946,090 A | 8/1999 | Tashiro et al. |
| 5,982,174 A * | 11/1999 | Wagreich ........... G01R 33/0322 250/227.17 |
| 6,097,488 A | 8/2000 | Grek et al. |
| 6,370,168 B1 | 4/2002 | Spinelli |
| 6,687,012 B2 * | 2/2004 | Sanzari .............. G01N 21/23 356/484 |
| 7,535,938 B2 | 5/2009 | Luo et al. |
| 7,817,325 B1 | 10/2010 | Uchikawa et al. |
| 7,991,028 B1 | 8/2011 | Bruno |
| 8,345,248 B2 * | 1/2013 | Hong .................. G01N 21/534 356/436 |
| 8,564,783 B2 | 10/2013 | Flanders et al. |
| 2004/0131092 A1* | 7/2004 | Nakayama ............ H01S 3/109 372/21 |
| 2005/0036534 A1* | 2/2005 | Baney ................ H01S 3/08004 372/106 |
| 2007/0047600 A1 | 3/2007 | Luo et al. |
| 2007/0064748 A1* | 3/2007 | Mirov ................ C30B 31/00 372/20 |
| 2007/0285669 A1* | 12/2007 | Ajgaonkar ........... A61B 5/0059 356/482 |
| 2009/0290167 A1 | 11/2009 | Flanders et al. |
| 2010/0265559 A1 | 10/2010 | Uchikawa et al. |
| 2011/0102565 A1 | 5/2011 | Wang et al. |
| 2012/0093179 A1 | 4/2012 | Dunn et al. |
| 2013/0088223 A1* | 4/2013 | Konno ................ G01R 33/032 324/244.1 |
| 2014/0055844 A1* | 2/2014 | Cormier ............ H01S 3/094042 359/341.3 |
| 2014/0204382 A1* | 7/2014 | Christensen .......... G01N 21/39 356/402 |
| 2014/0354275 A1* | 12/2014 | Sheng ................ G01R 33/26 324/244.1 |

FOREIGN PATENT DOCUMENTS

| | | |
|---|---|---|
| WO | 2005060056 A1 | 6/2005 |
| WO | 2005096115 A1 | 10/2005 |

OTHER PUBLICATIONS

Xiangmei, D., et al., A generation method of turnable cylindrical vector ring beam; Optics and Lasers in Engineering 50.12 (Dec. 2012); vol. 50, Issue 12; 2 pgs.

Kucera, P., et al.; Micropolarizers in Real Time Polariscope; 2011 21st International Conference Radioelektronika (Radioelektronika 2011); (Apr. 19-20, 2011); Piscataway, NJ, USA; 2 pgs.

Subrahmanyan, P., et al.; Simultaneous figuring and damage mitigation of optical surfaces; In Proceedings of the SPIE—The International Society for Optical Engineering (Sep. 22, 2008); USA; 2 pgs.

Zavattini, E.; Experimental observation of vacuum birefringence; Nuclear Physics B—Proceedings Supplements vol. 174 (Dec. 2007); 233-6; 2 pgs.

Riza, N.A.; et al.; Programmable spectral interferometric microscopy; Review of Scientific Instruments, vol. 76, Issue 3 (Mar. 2005): 33107-1-10; 2 pgs.

Cao, W., et al.; Mirrorless lasing in liquid crystalline materials; In Proceedings of the SPIE—The International Society for Optical Engineering; vol. 4642; 55-61; USA:SPIE-Int. Soc. Opt. Eng, 2002; 2 pgs.

Jackel, S., et al.; Adaptive compensation of lower order thermal aberrations in concave-convex power oscillators under variable pump conditions; Optical Engineering vol. 39, Issue 9 (Sep. 2000): 2330-7; 2 pgs.

Oakberg, T.C., et al.; A new instrument for measuring low level linear birefringence; In Conference on Lasers and Electro-Optics (CLEO 2000); Technical Digest Postconference Edition; TOPS vol. 39 (IEEE Cat. No. 00CH37088) Salem, MA; USA:Opt. Soc. America, 2000; 3 pgs.

Chauvat, D., et al.; Cotton-Mouton effect measurement with the Fabry-Perot eigenstates; Applied Physics Letters, vol. 73, Issue 8 (Aug. 24, 1998): 1032-4; 2 pgs.

Matzakos, P., et al.; New laser-based bistability system for optical computing applications; In Proceedings of the SPIE—The International Society for Optical Engineering , N. G., vol. 3423, 209-11. USA:SPIE-Int. Soc. Opt. Eng, 1998; 2 pgs.

Wilson, S.R., et al.; A simple apparatus for the measurement of the Cotton-Mouton effect in particulate suspensions; IEEE Transactions on Magnetics, vol. 33, Issue 5 (Sep. 1997): 4349-58; 2 pgs.

Cameron, R., et al.; Measurement of the magnetic birefringence of neon gas; Journal of the Optical Society of America B (Optical Physics), vol. 8, Issue 3 (Mar. 1991): 520-4; 2 pgs.

Kielich, S.; Nonlinear magnetooptics of colloids; Journal of Colloid and Interface Science vol. 30, Issue 2 (Jun. 1969): 159-76; 2 pgs.

* cited by examiner

METHOD AND SYSTEMS TO DETECT MATTER THROUGH USE OF A MAGNETIC FIELD GRADIENT

BACKGROUND

Determining the material composition of an unknown sample is useful for a variety of reasons. For example, determining the material composition of organic compounds present in biomarkers is of great interest to the pharmacy industry for the development of new medicines. Techniques traditionally used for determining material composition may include Raman and Luminescence Spectroscopy, X-ray Radiography, Tomography, Energy-Dispersive X-Ray Fluorescence (EDXRF), and Scanning Electron Microscope Energy-Dispersive Spectroscopy (SEM-EDS). Secondary Ion Mass Spectrometry (SIMS) and Laser-Ablation Inductively Coupled Plasma Mass Spectrometry (LA-ICP-MS) have also recently been applied in provenance determination studies. The aforementioned techniques however, suffer from a number of drawbacks. For example, many spectroscopic techniques are effective only at an atomic level of identification. Furthermore, many of the aforementioned techniques require a certain minimum amount of the test sample and are destructive in nature. In particular, some of the aforementioned spectroscopic techniques may, during examination, induce irreversible changes in the physical and chemical structure of the molecules comprising the test sample, thereby rendering it useless for future testing. It is with respect to these considerations and others that the various embodiments of the present invention have been made.

SUMMARY

This summary is provided to introduce a selection of concepts in a simplified form that are further described below in the Detailed Description. This summary is not intended to identify key features or essential features of the claimed subject matter, nor is it intended as an aid in determining the scope of the claimed subject matter.

Methods and systems for determining material composition of a test sample may be provided. The test sample may be placed in a magnetic region having a magnetic field. A light beam may be directed at the test sample in the magnetic region. A birefringence in the light beam that has passed through the test sample may be detected. The material composition of the test sample may be determined based on the detected birefringence in the light beam.

These and other features and advantages will be apparent from a reading of the following detailed description and a review of the associated drawings. It is to be understood that both the foregoing general description and the following detailed description are illustrative only and are not restrictive of the invention as claimed.

BRIEF DESCRIPTION OF DRAWINGS

The accompanying drawings, which are incorporated in and constitute a part of this disclosure, illustrate various embodiments of the present disclosure. In the drawings.

DETAILED DESCRIPTION

The following detailed description refers to the accompanying drawings. Wherever possible, the same reference numbers are used in the drawings and the following description to refer to the same or similar elements. While embodiments of the invention may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the invention. Instead, the proper scope of the invention is defined by the appended claims.

The disclosure provides methods and systems for determining a material composition of an unknown test sample. The disclosed systems and methods may provide a non-destructive way of determining the material composition of the test sample. The test sample may be placed in a magnetic region having a magnetic field. The magnetic field may induce contortions in the molecules of the test sample. A light beam may be passed through the test sample as a probe. The contortions in the test sample in the presence of the magnetic field may induce birefringence in the light beam. For examples, the light beam may split into two new light beams. The birefringence in the light beam may be measured by a detector. The detector then may determine the material composition of the test sample based on the measured birefringence. For example, the birefringence in the light beam may be indicative of the material composition of the test sample. The detector may compare the measured birefringence with standard values of birefringence stored in a database, and determine the material composition based on the comparison.

Figure 1:
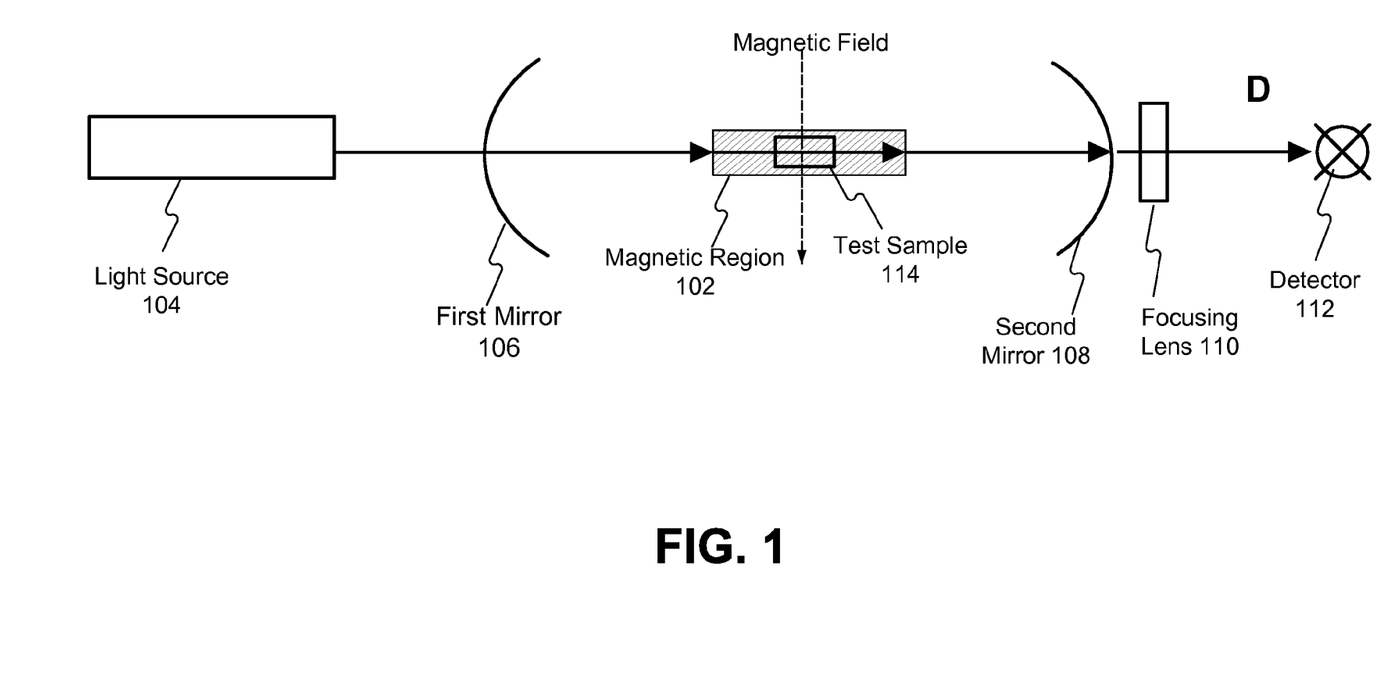
FIG. 1 is a diagram illustrating a system for determining the material composition of a test sample, in accordance with an embodiment.

FIG. 1 is a diagram illustrating a system 100 for determining the material composition of a test sample 114. In one implementation, the system 100 may determine the material composition of the test sample 114 by inducing contortions in the test sample 114 and using a light beam (generated from light source 104) to probe the contortions. As shown in FIG. 1, the system 100 may include the test sample 114, a magnetic region 102, the light source 104, a first mirror 106, a second mirror 108, a focusing lens 110, and a detector 112. In some embodiments, the system 100 may further include other elements such as depolarizers (not shown).

Magnetic region 102 of the system 100 may be a predefined region with a uniform magnetic field. An area of the magnetic region 102 may be predefined and controlled by a user of system 100. The magnetic field may be induced by permanent magnets or magnetic field inducing devices (not shown) placed around the magnetic region 102. In one implementation, the magnetic field in the magnetic region 102 may be an oscillating magnetic field. For example, the magnetic field may oscillate between a predetermined range. A rate of oscillation and a ramp rate of the oscillation of the magnetic field may be controlled by a user.

Light source 104 may provide a probe in the system 100. For example a light beam provided by the light source 104 may be sent to probe the test sample 114 in the magnetic region 102. In one implementation, the light source 104 may be a high intensity monochromatic light source such as a laser. In other implementations, alternative types of light sources (e.g., a tungsten lamp, a xenon flash lamp, etc.) coupled with wavelength selectors (e.g., acousto-optical tunable filters, monochromators, etc.) may also function as the light source 104. A frequency and intensity of the light beam originating out of the light source 104 may be controlled by the user. For example, the user may select different frequencies for the light beam originating out of the light source 104.

It should be understood that the first mirror 106 and the second mirror 108 may form an optical cavity. The optical cavity may be formed around the magnetic region 102. For example, the first mirror 106 and the second mirror 108 may be placed on either side of the magnetic region 102 at a predetermined distance thereby forming an optical cavity around the magnetic region 102. The first mirror 106 may also be located between the magnetic region 102 and light source 104. The light beam from the light source 104 may enter the optical cavity through an opening (not shown) in the first mirror 106. It should be understood that the first mirror 106 may be partially reflective in some implementations. Although the first mirror 106 and the second mirror 108 are shown to be concave mirrors, it should be apparent to those skilled in the art that the first mirror 106 and the second mirror 108 may alternatively be convex mirrors, planar mirrors, or any combination of concave, convex and planar mirrors. The optical cavity may be configured to enhance the birefringence induced in the light beam by reflecting the light beam into the test sample 114 multiple times.

Focusing lens 110 may be configured to focus the light beam exiting the optical cavity to the detector 112. The focusing lens 110 may be placed between the second mirror 108 and the detector 112. The light beam may exit the optical cavity via an opening (not shown) in the second mirror 108. It should be understood that the second mirror 108 may be partially reflective in some implementations. The focusing lens 110 may then direct the exiting light beam to detector 112 where it is collected. The detector 112 may be a device configured to measure the optical characteristics of the light beam that has passed through the test sample 114. For example, the detector 112 may be an optical detector such as a charge coupled device (CCD) camera, a photodiode, or a split photodiode. It should be appreciated by those skilled in the art that other devices may also be utilized to function as the detector 112. Additional details with respect to the detector 112 will be described below with respect to FIG. 3.

The test sample 114 may be an unknown material sample. For example, the test sample 114 may comprise a disease sample recovered from a patient. As another example, the test sample 114 may comprise an unknown explosive material. As a further example, the test sample 114 may comprise an unknown rock formation or a fossil. As a further example, the test sample 114 may comprise a chemical compound with an unknown molecular composition. It should be appreciated by those skilled in the art that many other types of material samples may also constitute the test sample 114 in various implementations.

Figure 2:
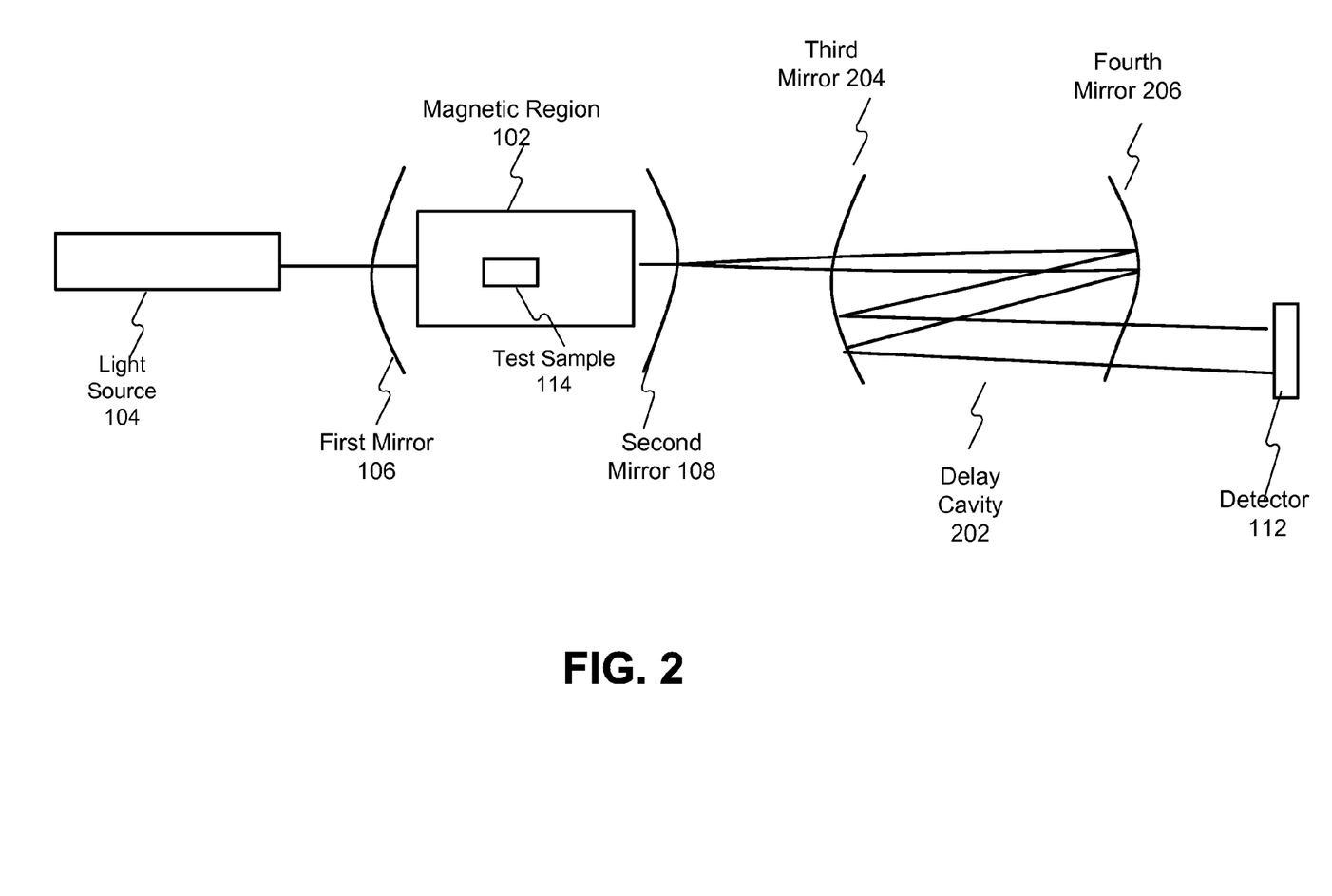
FIG. 2 is a diagram illustrating another system for determining the material composition of a test sample, in accordance with an alternative embodiment.

It should be understood that in an alternative embodiment, a path length of the light beam exiting the optical cavity may be incremented using a delay cavity. For example, FIG. 2 illustrates a system 200 for determining the material composition of the test sample 114 which includes a delay cavity 202. As shown in FIG. 2, the delay cavity 202 may include a third mirror 204 and a fourth mirror 206 facing the third mirror 204. A distance between the third mirror 204 and the fourth mirror 206 may be a predetermined distance. The third mirror 204 may include an opening (not shown) to admit the light beam (from the light source 104) into the delay cavity 202. In addition, the fourth mirror 206 may also include an opening (not shown) to allow the light beam to exit the delay cavity 202. Although the third mirror 204 and the fourth mirror 206 of the delay cavity 202 are shown to be concave mirrors, it should be appreciated by those skilled in the art that the third mirror 204 and the fourth mirror 206 may alternatively be convex mirrors, planar mirrors, or any combination of concave, convex or planar mirrors.

The light beam from the light source 104 may enter the delay cavity 202 through the opening in the third mirror 204 and be directed toward the fourth mirror 206. The fourth mirror 206 may reflect the light beam back in the delay cavity 202 towards the third mirror 204. The third mirror 204 may again reflect the light beam back in the delay cavity 202 towards the fourth mirror 206. As a result, the light beam may be reflected back and forth between the third mirror 204 and the fourth mirror 206 in the delay cavity 202 for a predetermined number of times. It should be understood that the back-and-forth reflection of the light beam between the third mirror 204 and the fourth mirror 206 may enhance the path length of the light beam that has passed through the test sample 114. The enhancement in the path length may also result in enhancement of the birefringence in the light beam. The light beam may exit the delay cavity 202 after a predetermined number of traversals and then be collected by the detector 112.

Figure 3:
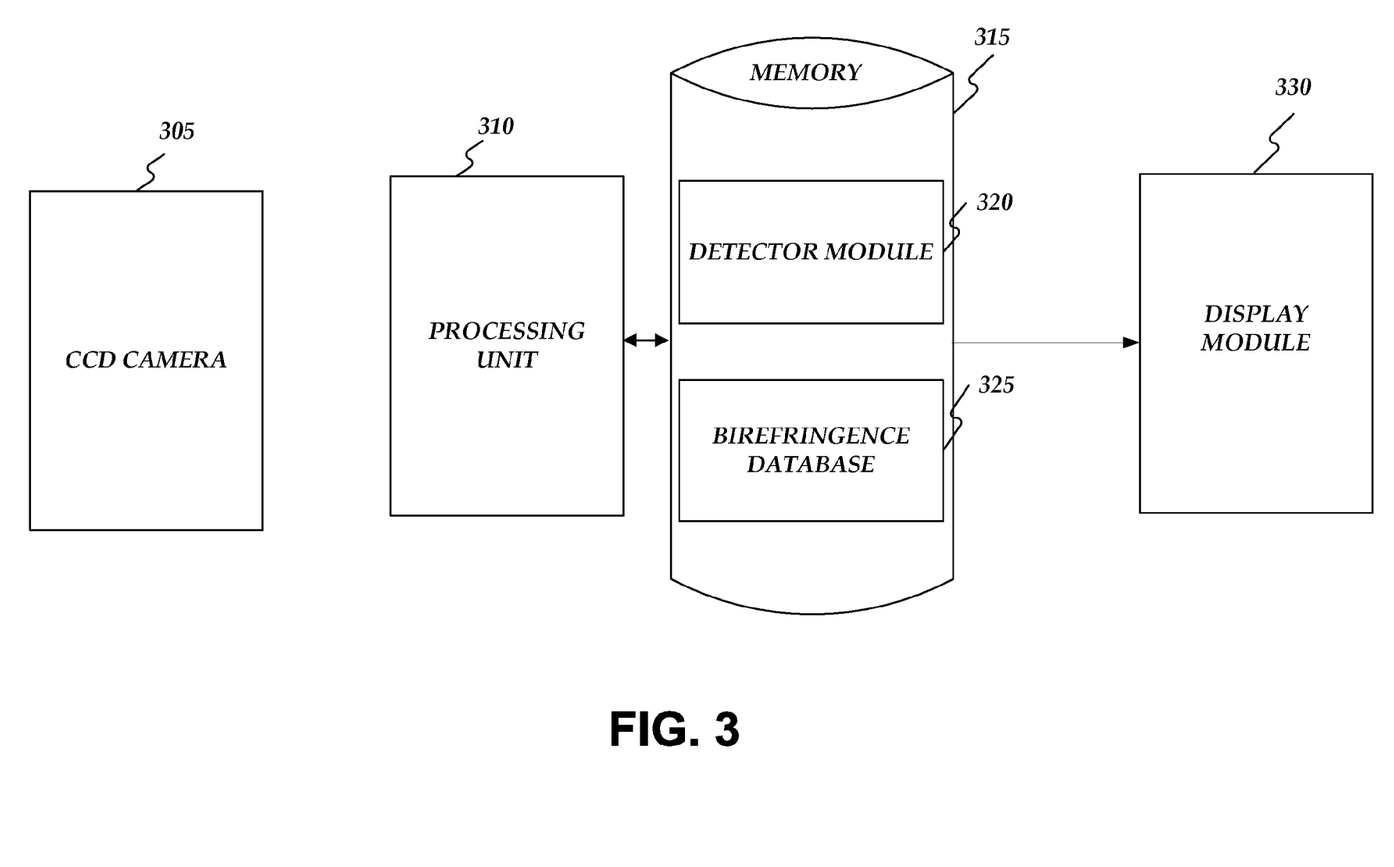
FIG. 3 is a diagram illustrating a detector of a system for determining the material composition of a test sample, in accordance with an embodiment.

FIG. 3 shows the detector 112 in greater detail. As shown in FIG. 3, the detector 112 may include a charge coupled device (CCD) camera 305, a processing unit 310, a memory unit 315, and a display module 330. In one implementation, the CCD camera 305 may be an optical device configured to measure the optical characteristics of the light beam that has passed through test sample 114. For example, the CCD camera 305 may measure an angle of split in the light beam as a change in the central energy deposited), a waist of the light beam (i.e., beam waist), a number of photons in the light beam, energy in the light beam, etc. Although the detector 112 is shown to include CCD camera 305, it should be understood by those skilled in the art that other optical sensors, such as a photodiodes and split-photodiodes, may be used in place of the CCD camera 305.

Memory Unit 315 may include a detector module 320 and a birefringence database 325. While executing on the processing unit 310, the detector module 320 may perform a method for identifying the material composition of a test sample, including, for example, one or more stages included in method 400 described below with respect to FIG. 4. The results of the determination made by the detector module 320 may be displayed on the display module 330.

Figure 4:
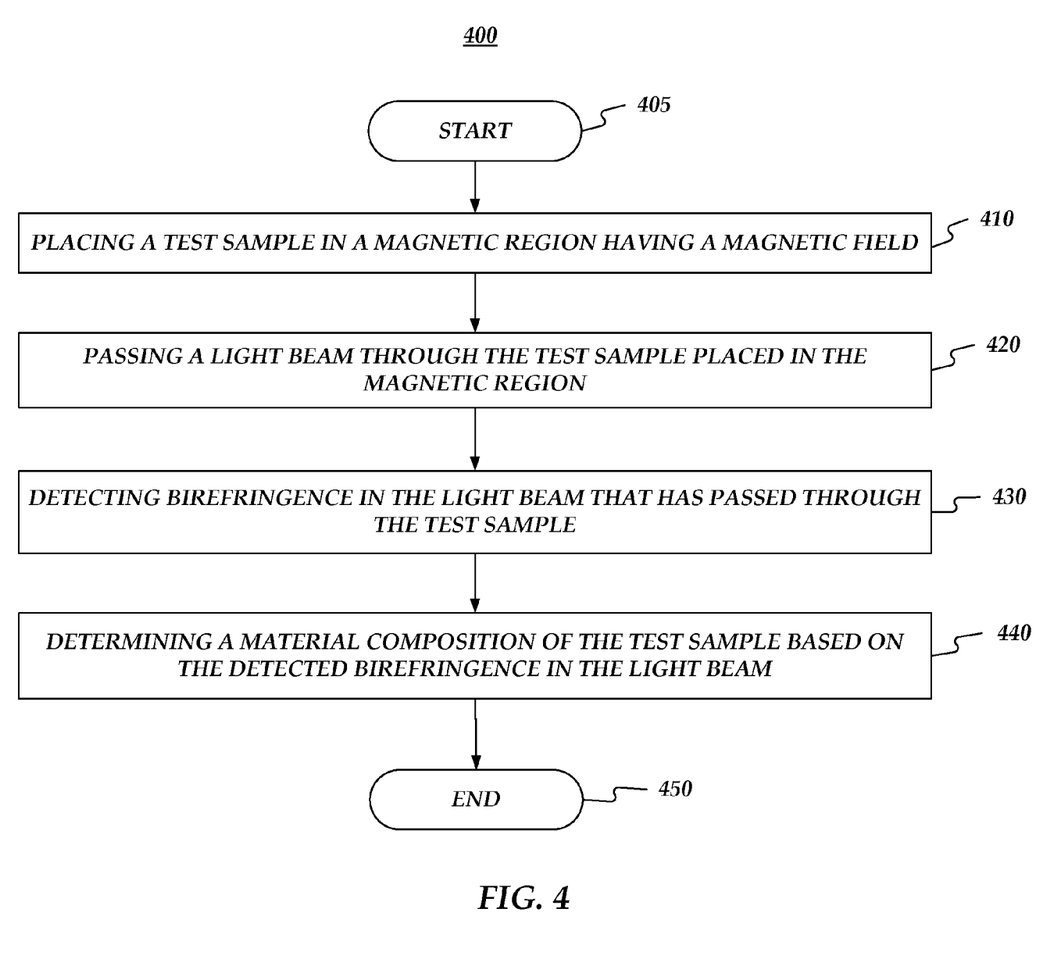
FIG. 4 is a flow diagram illustrating a method for determining the material composition of a test sample, in accordance with an embodiment.

FIG. 4 is a flow diagram setting forth the general stages involved in a method 400 consistent with an embodiment of identifying the material composition of the test sample 114 described above with respect to FIGS. 1 and 2. The method 400 may be implemented using the systems 100 and 200 as described above with respect to FIGS. 1 and 2, respectively. Implementation of the various stages of the method 400 will be described in greater detail below.

The method 400 may begin at starting block 405 and proceed to stage 410 where the test sample 114 may be placed in the magnetic region 102. For example, the test sample 114 may be placed at the center of the magnetic region 102. The test sample 114 may be placed in the magnetic region 102 in any of solid, liquid or gaseous states.

It should be understood that in some embodiments, only a very small amount (relative to a total mass) of the test sample 114 may be placed in the magnetic region 102. For example, the amount of test sample 114 required by the system 100 may be less than the amount typically utilized for tests using spectroscopic or X-ray techniques. The magnetic field of the magnetic region 102 may induce contortions in the test sample 114. For example, the magnetic field may induce expansion and/or contraction in the molecules of the test sample 114. The contortions in the test sample 114 may be induced because the molecules of test sample 114 may include charge particles. These charge particles may respond to the magnetic field by inducing contraction or expansion in the test sample 114.

A rate of contortion and an amount of contortions in the test sample 114 may directly be related to the strength of the magnetic field and the ramp rate of the oscillating magnetic field. Hence, the contortions in the test sample 114 may be controlled by controlling the ramp rate of the oscillation of the magnetic field in the magnetic region 102. For example, the ramp rate may be controlled such that the test sample 114 is not destroyed by the induced contortions during testing. Hence, the material composition of the test sample 114 may be determined without altering the physical or chemical properties of the test sample 114. For example, the ramp rate and the amount of the magnetic field may be controlled such that the contortions induced in the molecules of the test sample 114 may be temporary, and the molecules may return to their original physical state after testing. Hence, the systems 100 and 200 described above may be utilized to determine the material composition of the test sample 114 in a non-destructive manner thereby allowing the test sample 114 to be reused for further testing.

From stage 410, where the test sample 114 may be placed in the magnetic region 102, the method 400 may advance to stage 420 where a light beam (provided by the light source 104) may be passed through the test sample 114 placed in the magnetic field. The light beam may pass through the test sample 114 in a direction perpendicular to a direction of the magnetic field of the magnetic region 102. The light beam when passing through the test sample 114 may experience birefringence. As should be understood by those skilled in the art, birefringence is a phenomenon of double refraction whereby the light beam, when incident upon the test sample 114, is split by polarization into two beams taking slightly different paths. The birefringence of the light beam may be caused by a magneto-optical phenomenon (also referred to as the Faraday Effect) which is caused by an interaction between the light beam and the magnetic field of the magnetic region 102. The Faraday Effect may cause a rotation in a plane of polarization which may be proportional to a component of the magnetic field in the direction of propagation. The Faraday Effect may further induce other measurable changes in the light beam, such as loss of photons, expansion of waist (i.e., beam waist), loss of energy, etc.

In one embodiment, an angle of split or rotation in the light beam may depend on a frequency of the light beam, the material composition of the test sample 114, and a ramp rate of the oscillating magnetic field in the magnetic region 102. Thus, with respect to the test sample 114, a data set of the birefringence may be obtained by varying the frequency of the light beam as well as the strength of the magnetic field of the magnetic region 102. Since, the ramp rate of the oscillating magnetic field may be much slower than the speed of the light beam, birefringence for each of a number of values of the magnetic field may be recorded. In one implementation, the system 100 may further include depolarizers (not shown) located on either side of the magnetic region 102. The depolarizers may be configured to scramble new light beams produced because of birefringence in the original light beam such that each time the light beam passes through the test sample 114, all of the new light beams that are subsequently produced have essentially a fixed polarization.

In one implementation, the birefringence in the light beam may be enhanced by the optical cavity of the system 100. The light beam originating from the light source 104 may enter the optical cavity through an opening in the first mirror 106. The light beam may travel through the magnetic region 102 passing through the test sample 114 to the second mirror 108. The second mirror 108 may then reflect the light beam back into the magnetic region 102 through the test sample 114 to the first mirror 106. Thus, the light beam may be reflected in the optical cavity multiple times, with reach reflection passing through the test sample 114. Since, the light beam is split into two new beams each time it passes through the test sample 114 (under the influence of depolarizers), the optical cavity may contain multiple light beams after multiple passes.

Once, the light beam has passed through the test sample 114 at stage 420, the method 400 may advance to stage 430 where the birefringence in the light beam may be detected. For example, the birefringence in the light beam may be detected by the detector 112. The light beam may be collected at the detector 112 through the focusing lens 110. In particular, the second mirror 108 may include an opening which may allow the light beam to exit the optical cavity to the focusing lens 110. The focusing lens 110 may then direct the light beam to the detector 112. The light beam may be collected at the detector 112 at a predetermined interval or after a predetermined number of traversals through the test sample 114.

In one embodiment, a path length of the light beam may be enhanced by the delay cavity 202 to enhance the birefringence before the light beam is collected at the detector 112. For example, the light beam exiting the optical cavity may be directed into the delay cavity 202 through the opening in the third mirror 204. The light beam may be reflected by the third mirror 204 and the fourth mirror 206 in the delay cavity 202 for a predetermined number of times. After a predetermined number of traversals in the delay cavity 202, the light beam may be collected at the detector 112.

The detector 112 may be configured to measure birefringence in the light beam. The birefringence may be determined by measuring an angle of split in the light beam. In addition to detecting the birefringence, the detector 112 may be configured to measure other optical characteristics of the light beam. For example, the detector 112 may also measure a beam diameter, a beam separation parameter, energy loss and number of transitions in the light beam. As will be discussed in greater detail below, the detector 112, based on the detected birefringence in the light beam, may then identify the material composition of the test sample 114.

From stage 430, where the birefringence in the light beam has been detected by the detector 112, the method 400 may advance to stage 440 where a material composition of the test sample 114 may be determined by the detector 112 based on the detected birefringence in the light beam. For example, the detector module 320 may compare the birefringence detected for the test sample 114 with a reference birefringence value from the birefringence database 325 to determine the material composition of the test sample 114.

The detector module 320 may be configured to compare the values of the birefringence in the light beam detected on the CCD camera 305 with the values stored in the birefringence database 325. The birefringence database 325 may comprise stored reference birefringence values of known material compositions or molecules at different frequencies of the light beam and different magnitudes of the magnetic field. The detector module 320 may then compare the birefringence values detected by CCD camera 305 with the reference birefringence values stored in the birefringence database 325 and determine the material composition matching the detected birefringence values. In one embodiment, the detector 112 may be connected to a computer system having an access to the aforementioned reference birefringence values. The computer system may be configured to compare the detected values with the reference values. In another embodiment, the detector 112 may be configured to display the detected birefringence on the display module 330. For example, the detector 112 may display the detected birefringence at the display module 330 and a user may manually compare the detected birefringence with standard birefringence values to determine the material composition of the test sample 114. The birefringence values of the test sample 114 may be displayed on the display module 330 in the form of a table, a graph, or a data set. Similarly, the material composition of the test sample 114 may be displayed on the display module 330 as a common name, scientific name, molecular structure, or a combination thereof. Once the material composition of the test sample 114 has been determined by the detector 112 at stage 440, the method 400 may end at stage 450.

In one embodiment, the systems and methods described above may be utilized to determine a material composition in biomarkers of a disease sample in a non-destructive manner, thereby allowing the disease sample to be utilized for further testing. The systems and method may further be utilized to provide a molecular composition of the biomarkers. For example, the systems and method may provide a molecular composition of cancer cells recovered from patients. In another embodiment, the systems and methods may be utilized to determine whether a suspect sample is an explosive substance.

While the specification includes examples, the disclosure's scope is indicated by the following claims. Furthermore, while the specification has been described in language specific to structural features and/or methodological acts, the claims are not limited to the features or acts described above. Rather, the specific features and acts described above are disclosed as examples for embodiments of the disclosure.

What is claimed is:

1. A method of determining a material composition of a test sample, the method comprising:
   receiving the test sample in a magnetic region having an oscillating magnetic field, wherein the magnetic region is in an optical cavity comprising at least a first mirror and a second mirror facing the first mirror, wherein the oscillating magnetic field has a ramp rate and is configured to induce contortions that alter at least one of a physical and a chemical composition of the test sample;
   passing, by a light source, a light beam through the test sample in the magnetic region;
   detecting, at a detector device, birefringence in the light beam that has passed through the test sample; and
   determining, by a processing unit, the material composition of the test sample based on the detected birefringence in the light beam, wherein determining the material composition of the test sample comprises reducing the contortions by controlling the ramp rate of the oscillating magnetic field, wherein the altered at least one of the physical and chemical composition of the test sample is returned to an original state in response to controlling the ramp rate of the oscillating magnetic field.

2. The method of claim 1, wherein detecting birefringence in the light beam that has passed through the test sample further comprises:
   enhancing the birefringence induced on the light beam by the test sample by using the optical cavity, wherein the first mirror and the second mirror are configured to enhance the birefringence by reflecting the light beam in the optical cavity for a predetermined number of times;
   collecting the light beam at a predetermined interval at the detector device during the light beam being reflected back in the optical cavity; and
   determining the birefringence in the light beam at the predetermined regular interval.

3. The method of claim 2, wherein reflecting the light beam in the optical cavity comprises reflecting the light beam through the test sample for the predetermined number of times.

4. The method of claim 1, wherein determining the material composition of the test sample based on the determined birefringence in the light beam comprises:
   comparing the detected birefringence with reference values of the birefringence stored in a reference database; and
   determining the material composition of the test sample based on the comparison.

5. The method of claim 1, wherein passing the light beam comprises passing the light beam perpendicular to a direction of the magnetic field.

6. A system comprising:
   an optical cavity comprising a first mirror and a second mirror facing the first mirror;
   a magnetic region having an oscillating magnetic field configured to induce contortion in a test sample in the magnetic region, wherein the oscillating magnetic field has a ramp rate and the contortion alters at least one of a physical and a chemical composition of the test sample;
   a light emitting device configured to emit a light beam to pass through the test sample in the magnetic field;
   a detector configured to detect birefringence in the light beam that has passed through the test sample and the mirror cavity; and
   a processing unit, in communication with the detector, wherein the processing unit is configured to determine a material composition of the test sample based on the detected birefringence in the light beam, and the material composition of the test sample is determined by reducing the contortion, wherein the contortion is reduced by controlling the ramp rate of the oscillating magnetic field, wherein the altered at least one of the physical and chemical composition of the test sample is returned to an original state in response to controlling the ramp rate of the oscillating magnetic field.

7. The system of claim 6, wherein the magnetic field is in the optical cavity, and wherein the optical cavity is configured to reflect the light beam passed through the test sample back to the test sample.

8. The system of claim 7, wherein the detector is further configured to detect birefringence in the light beam after the light beam has passed through the test sample a predetermined number times.

9. The system of claim 6, wherein the detector is further configured to detect at least one of: a photon density, a beam diameter, and an energy loss in the light beam that has passed through the test sample.

10. The system of claim 6, wherein the magnetic field is perpendicular to a direction of propagation of the light beam.

11. The system of claim 6, wherein the first mirror and the second mirror are at least one of: a concave mirror, a convex mirror, a planar mirror, and a combination thereof.

12. The system of claim 6, further comprising a delay cavity, wherein the delay cavity is configured to enhance a path length of the light beam that has passed through the test sample by reflecting the light beam a predetermined number of times inside the delay cavity.

13. The system of claim 12, wherein the delay cavity comprises a third mirror and a fourth mirror placed at a predetermined distance from the third mirror, wherein the third mirror and the fourth mirror are facing each other.

14. The system of claim 6, wherein the test sample is a biomarker related to a disease.

15. The system of claim 14, wherein the processing unit is further configured to identify the material composition of the biomarker related to the disease based on the birefringence properties of the biomarker.

* * * * *